United States Patent
Golz et al.

[11] Patent Number: 5,951,967
[45] Date of Patent: Sep. 14, 1999

[54] MULTI-PHASE LIGHT SCREENING AGENT, PROCESS FOR ITS PRODUCTION AND FOR ITS APPLICATION TO THE SKIN

[75] Inventors: Karin Golz; Leonhard Zastrow, both of Monaco, Monaco; Klaus Stanzl, White Plains, N.Y.; Jacques Gerbron, Menton; Louis Ferrero, Nice, both of France

[73] Assignee: Lancaster Group GmbH, Ludwigshafen, Germany

[21] Appl. No.: 08/973,605

[22] PCT Filed: Jun. 7, 1996

[86] PCT No.: PCT/DE96/01046

§ 371 Date: Jan. 28, 1998

§ 102(e) Date: Jan. 28, 1998

[87] PCT Pub. No.: WO96/41613

PCT Pub. Date: Dec. 27, 1996

[30] Foreign Application Priority Data

Jun. 8, 1995 [DE] Germany ............................ 195 21 951

[51] Int. Cl.$^6$ ................ A61K 7/42; A61K 7/44; A61K 7/00

[52] U.S. Cl. ................ 424/59; 424/60; 424/401

[58] Field of Search .................. 424/59, 60, 401

[56] References Cited

U.S. PATENT DOCUMENTS

| | | | |
|---|---|---|---|
| 5,213,799 | 5/1993 | Goring et al. | 424/401 |
| 5,468,496 | 11/1995 | Touzan et al. | 424/401 |

FOREIGN PATENT DOCUMENTS

| | | |
|---|---|---|
| 0 588 498 | 3/1994 | European Pat. Off. . |
| 0 619 999 | 10/1994 | European Pat. Off. . |
| 0 603 080 | 6/1994 | Germany . |
| 4 426 952 | 10/1995 | Germany . |
| WO94/17779 | 8/1918 | WIPO . |
| WO94/22419 | 10/1994 | WIPO . |

*Primary Examiner*—Shelley A. Dodson
*Assistant Examiner*—Marina Lamm
*Attorney, Agent, or Firm*—Collard & Roe, P.C.

[57] ABSTRACT

A multi-phase sunscreen agent, characterized by at least two phases that are liquid to pasty or gelatinous and separate from each other spontaneously within seconds to less than ten minutes after a brief and gentle mixing process lasting less than one minute without any essential application of force, where at least one phase contains a UV filter.

19 Claims, No Drawings

MULTI-PHASE LIGHT SCREENING AGENT, PROCESS FOR ITS PRODUCTION AND FOR ITS APPLICATION TO THE SKIN

BACKGROUND OF THE INVENTION

1. Field of the Invention

The invention concerns a new multi-phase sunscreen agent with improved sunscreen properties.

2. The Prior Art

A multitude of sunscreen formulations are already known that contain certain organic and inorganic active ingredients as emulsions for filtering out (absorption or reflection) UVB radiation (range 290 to 320 nm) and UVA radiation (range 320 to 400 nm). Known organic active ingredients include in particular the derivatives of dibenzoylmethane, benzophenone, salicylic acid, cinnamic acid, 3-benzylidenecamphor, 4-aminobenzoic acid, etc. Known inorganic active ingredients include pigments such as the oxides of titanium, iron, zinc, silicon, aluminum, zirconium, etc. A mixture of organic and inorganic substances that is described as being superior to titanium dioxide is also known (European Patent EP A 588,498).

Published International Application No. WO 94/22419 describes a skin tanning agent where two components are present in separate containers and react when mixed together on the skin, producing a color.

The development of sunscreen formulations has mainly tended toward new active ingredients or a combination of known active ingredients. In general, these are present in emulsions to ensure a good and uniform distribution on the skin, where agglomerations of inorganic pigments have been prevented by surface-active substances.

However, hydrodispersions have also become known that do not contain any emulsifier and are a dispersion of a discontinuous lipid phase (liquid, solid or semisolid) in an external continuous (aqueous) phase. The stability of such an emulsifier-free system is achieved, for example, by creating a gel structure in the aqueous phase with a stable suspension of the lipid droplets in this gel structure. A disadvantage of these hydrodispersions is the required high concentration of UV filter materials and their stickiness.

European Patent EP A 603,080 describes a cosmetic or dermatological two-phase composition that consists of an aqueous phase and a separate oil phase containing alkyldimethylbenzyl-ammonium chloride in the aqueous phase and is suitable for skin care or for removing make-up.

World Patent WO 94/17779 discloses hydrodispersions which are emulsifier-free products to prevent possible irritating effects of emulsifiers (Mallorca acne). The stability of the dispersions is supposed to be ensured by an internal lipid phase with the inorganic pigments and an external aqueous phase.

SUMMARY OF THE INVENTION

The object of this invention is to achieve an improvement in the sunscreen properties through a particular arrangement of these agents in a formulation system and to prevent the chemical filters from coming directly in contact with the skin.

According to this invention, the new sunscreen consists of at least two separate and essentially liquid phases, where UVA and/or UVB filters and/or UVC filters (hereinafter: UV filters) are present in at least two separate phases, where the phases separate spontaneously after a brief and gentle mixing process, leaving the respective UV filters in the phase in which they were originally present.

It has been found that by spreading one of the separate phases on the skin and applying at least one second phase above it, where the second phase essentially does not mix with the first phase and each phase contains a UV filter, improved absorption of UV radiation is achieved in comparison with an emulsion or hydrodispersion containing the same amount of these UV filters. When converted to a sunscreen factor, this means an increase by at least two stages, preferably four to ten stages.

However, an improvement in the sunscreen factor is achieved even if only one phase contains a UV filter and the other phase does not contain any UV filter but contains different substances from the first phase, because the depth of penetration and the refraction of incident radiation differ according to the thickness of the layer and possibly the type of layer.

The sunscreen agent according to this invention consisting of at least two separate phases, preferably three of more phases, can be applied to the skin, where it develops these phases spontaneously again after application. This means that by rubbing the complete sunscreen agent removed from a storage container, the mixing process causes only an a momentary mixing effect which is then eliminated again almost completely due to the type of phases selected and their physical properties. The phase separation yields a layering effect of the sunscreen on the skin. The UV filters are selected so that after mixing, they are present again in the respective phase (layer) in which they were originally present, i.e., before the mixing process.

A preferred composition is, for example, the following, based on the skin surface:

(A) a phase that is directly against the skin and contains one or more fluorocarbons and an inorganic pigment as a UV filter;

(B) a phase above that, consisting of a polymer lacquer or a polymer film-forming compound in an organic solvent (hereinafter: polymer lac), optionally in mixture with a UV filter; and (C) an oily phase above that, also containing a UV filter.

The proportion of phases, based on the total composition in such an example of a composition amounts to approximately: 15 to 35 wt % phase (A); 5 to 25 wt % phase (B); and 25 to 80 wt % phase (C).

Additional phases may also be included in the sunscreen agent, e.g., another oily phase (D) in the form of a silicone oil, optionally containing a lipophilic UV filter, as well as other phases.

With a layered structure having three or more phases, a phase consisting preferably of a polymer lac in a suitable solvent that is gentle to the skin is provided between an oily layer and a non-oily layer, for example. Shellac is an example of such a lac.

Shellac is a natural resin of animal origin with an average molecular weight of 1000 g/mol. It consists mainly of hydroxycarboxylic acids that are partially unsaturated, contain aldehyde groups and are in ester or lactone form. It has good compatibility with other resins, polymers and additives and is physiologically and toxicologically safe.

An example of a suitable polysiloxane copolymer that may be present in an oily phase would be poly (dimethylsiloxane) and poly(isobutyl methacrylate), a copolymer of poly(dimethylsiloxane) and polyacrylate, a copolymer of poly(dimethylsiloxane) and poly(isobutyl methacrylate)-containing copolymers (e.g., SA 70-5 from 3M Company, USA).

A suitable non-oily phase is preferably a phase containing fluorocarbons, especially perfluorocarbons. Perfluorocarbons that can be used include perfluorodecalin, perfluorotributylamine, perfluorooctyl bromide, bisfluoro (butyl)ethene or $C_6$-$C_9$-perfluoroalkanes and mixtures of these together and/or with perfluoropolyethers. A preferred perfluorocarbon is perfluorodecalin. A mixture of perfluorodecalin and perfluoropolymethylisopropyl ether is especially preferred. UV filters such as inorganic oxides or melanin are suspended in it. The viscosity of such a phase can be adjusted easily on the basis of the molecular weight of the perfluoropolyether.

The perfluorocarbons themselves are completely non-toxic and are very stable with respect to external influences such as physical and chemical influences (organic solvents, acids, alkali, UV radiation, temperature).

An advantageous mixing ratio of the mixture mentioned as especially preferred is in the range of 1.5-3:3-1.5.

A preferred phase composition may essentially be free of water.

The phase separation can be attributed to the different types of phase-forming basic ingredients or to definite differences in such physical properties as density and hydrophilic or hydrophobic properties. In general, a pronounced phase interface develops with each phase, preferably extending over the entire interface of the other phase without interruption, i.e., the development of droplets or individual fields is avoided. The phases used according to this invention are essentially not miscible with one another and thus are separate from each other. This condition is usually stable for the period of time immediately after mixing the phases until a few minutes thereafter, preferably a few hours thereafter.

A single UV filter is present in the most homogeneous possible distribution in the respective phases. Such a UVB filter may be, for example:

a salicylic acid ester, such as 2-ethylhexyl salicylate, menthyl salicylate, 4-isopropylbenzyl salicylate;
 a benzophenone such as 2-hydroxy-4-methoxybenzophenone;
 a 4-aminobenzoic acid ester, such as 2-ethylhexyl 4-(dimethylamino)benzoate, amyl 4-(dimethylamino)benzoate;
 a 3-benzylcamphor derivative, such as 3-(4-methylbenzylidene)camphor or 3-benzylidenecamphor;
 a cinnamic acid ester, such as 2-ethylhexyl 4-methoxycinnamate or isopentyl 4-methoxycinnamate; or
 a benzomalonic acid ester or a triazine.

A combination with UVA filters such as dibenzoylmenthane derivatives such as 1-(4'-tert-butylphenyl)-3-(4'-methoxyphenyl)-1,3-propanedione or 1-phenyl-3-(4'-isopropylphenol)-1,3-propanedione may also be advantageous.

The above-mentioned UV filters are lipophilic and therefore are suitable for incorporation into one or more of the oily phases. These phases may preferably also contain free radical scavengers such as vitamin E.

A hydrophilic UV filter may also be incorporated into the non-oily phase to advantage. Hydrophilic UV filters include: sulfonic acid derivatives of benzophenones such as 2-hydroxy-4-methoxybenzophenone-5-sulfonic acid and the salts thereof; 2-phenylbenzimidazole-5-sulfonic acid and the salts thereof; 3-benzylidenecamphorsulfonic acids such as 4-(2-oxo-3-bornylidenemethyl)benzenesulfonic acid, etc. and salts thereof.

The non-oily phase may advantageously contain inorganic pigments such as titanium dioxide and zinc oxide and mixtures thereof with aluminum oxide and/or silicon dioxide as UV filters. This is a special measure according to this invention that yields the advantage that the user has no problems with allergic irritation due to chemical UV filters when inorganic pigments are provided in the phase next to the skin. Titanium dioxide is especially preferred.

The particle size of the inorganic pigments is preferably less than 400 nm, especially less than 300 nm. Natural pigments such as melanin may also be used.

The sunscreen agent according to this invention will generally contain lipophilic filters in the oily phase and hydrophilic filters in the non-oily phase. With a three-layer or multi-layer composition, UV filters may also be present in one or two other phases between these oily and non-oily phases. These filters are preferably different from the neighboring phases to ensure that the UV filter provided for the intermediate phase is again present in this layer even when the phases separate after the mixing process. This type of filter may be different, depending on the filters in the neighboring phases, and is to be selected by those skilled in the art, taking into account the above factors.

Of course, several UV filters may also be present in one phase, assuming at least one other UV filter is present in a second phase.

It has surprisingly been found in the layering of several separate phases one above the other according to this invention that:

the absorption of two UV filters, each separately in a homogeneous phase (layer), is much greater than the absorption of the same filters in mixture with each other in just one phase, assuming the same concentrations;
 the absorption is greater, the more homogeneously the filters are distributed and the thicker the layer;
 any negative effect of the organic filters (chemical filters) on sensitive skin is prevented by the arrangement of one layer directly on the skin surface with inorganic pigments alone (so-called physical filters), and thus there are no allergic reactions;
 1. this yields a reduced usage of the active ingredient (UV filter) with a separate layered composition of a sunscreen agent in comparison with the conventional emulsion, or a higher sunscreen factor is obtained with the same quantity of active ingredient;
 a pleasant, soft feeling on the skin is obtained without any stickiness;
 large amounts of inorganic pigments such as $TiO_2$ do not lead to any whitening effect, i.e., there is no white streaking on contact with water.

Another advantage of the present invention with a multilayer composition including a layer with a polymer lac is that the water resistance of the sunscreen agent is greatly improved. This is an important advance, especially for sunscreen agents, because it eliminates the repeated application of the agent to the skin when swimming in swimming pools or natural bodies of water. It has been found that a single application of the agent and repeated swimming thereafter provides protection for at least three to four hours without a single repeat application.

This invention also concerns a process for producing a sunscreen agent that is characterized in that at least two separate, essentially liquid phases, at least one of which contains a UV filter, but preferably two phases contain a UV filter, are placed in a container. The phases in the container are separate from each other in the container or are spatially separated; the phases are preferably spatially separated from each other.

"Essentially liquid phases" in the sense of the present invention is understood to refer to substances that are liquid to pasty or gelatinous and can be distributed uniformly when applied to the skin.

"Non-miscible phases" in the sense of the present invention is understood to refer to substances that are difficult or impossible to mix or spread on each other, whether with or without the addition of any additives, without forming an essential mixed phase. The condition of non-miscibility with each other and the liquids is based on the temperature range of 5° C. to 50° C., i.e., normally ambient temperature.

Phases "separate from each other" are those that form layers when layered one above the other or when mixed gently together. "Spatially separated" phases are those that are arranged without any direct contact with each other.

"Brief and gentle mixing process" is understood to be a mixing process that takes less than approximately one minute and involves essentially no application of force, e.g., by allowing the phases to flow into each other and/or by rubbing the phases on the skin.

"Spontaneously separating" is understood to mean that layers develop within seconds to less than ten minutes after a brief and gentle mixing process.

The process according to this invention for applying a sunscreen to the skin consists of mixing essentially liquid phases that are separate in a dispenser or are spatially separated, with UVA and/or UVB filters being present in at least two separate phases, in predetermined mixing ratios immediately before application and then applying them to the skin in mixed form and distributing them.

A preferred method of applying the sunscreen agent consists of briefly and gently mixing, immediately before application, essentially liquid and anhydrous phases that are spatially separated from each other in a dispenser and consist of at least:

(1) an oily phase containing a UV filter,
(2) a phase consisting of a polymer lac or a polymer film-forming compound in an organic solvent and optionally containing a UV filter,
(3) a phase containing one or more fluorocarbons and an inorganic pigment as UV filters, in predetermined mixing ratios and applying them in mixed form to the skin and distributing them there.

A dispenser for applying the sunscreen agent according to this invention may be, for example, a container that has three compartments and is or can be pressurized and contains, for example, the individual phases in predetermined quantities in these chambers. These phases are then mixed together in the desired mixing ratio in a mixing head by operating the pressure valve and are dispensed through an outlet orifice. Following this, they are distributed on the skin by the user.

DETAILED DESCRIPTION OF PREFERRED EMBODIMENTS

The invention will be explained in greater detail below on the basis of examples. All percentages are based on weight (wt %) unless otherwise indicated.

The individual phases are prepared by dispersing the inorganic pigment, e.g., $TiO_2$, and optionally a coloring pigment in the liquid medium for phase A. For phase B, the polymer lac or film-forming agent and optionally the chemical UV filters are added to the solvent and mixed. For phase C or other phases, chemical filters are added to the liquid oils or silicone polymers, optionally also in combination with antioxidants such as vitamin E, and mixed together.

EXAMPLE 1

The individual phases were prepared separately by mixing the respective ingredients in the manner indicated above.

| Phase A | |
| --- | --- |
| Perfluorodecalin | 60% |
| Perfluoropolymethylisopropyl ether (Fomblin HC) | 30% |
| UV filter $TiO_2$ | 10% |
| Phase B | |
| Shellac | 1.0% |
| UV filter benzophenone-3 (2-hydroxy-4-methoxybenzophenone) | 2.0% |
| UV filter octyl methoxycinnamate (2-ethylhexyl p-methoxycinnamate) | 4.5% |
| Isopropanol | QS |
| Phase C | |
| Jojoba oil | 5.0% |
| UV filter benzophenone-3 | 6.0% |
| Vitamin E | 1.0% |
| UV filter octyl methoxycinnamate | 5.5% |
| Dioctyl ether | QS |

The proportions of phases A, B and C in the total mixture were 35%, 20% and 45%, respectively.

EXAMPLE 2

The individual phases were prepared separately by mixing the respective ingredients in the proper manner.

| Phase A | |
| --- | --- |
| Perfluorodecalin | QS |
| UV filter $TiO_2$ | 8% |
| Zinc oxide | 7% |
| Kaolin/silicon dioxide | 10% |
| Phase B | |
| Shellac | 3.0% |
| UV filters, sodium and triethanolamine salts of 2-phenylbenzimidazole-5-sulfonic acid | 20.0% |
| UV filter octyl methoxycinnamate | 4.5% |
| Ethanol | QS |
| Phase C | |
| Jojoba oil | 7.5% |
| Isohexadecane | 3.5% |
| Vitamin E | 1.0% |
| UV filter octyl methoxycinnamate | 15.5% |
| Oxybenzone | 9.5% |
| Dioctyl ether | QS |

The proportions of phases A, B and C in the total mixture were 15%, 5% and 80%, respectively.

EXAMPLE 3

The individual phases were prepared separately by mixing the respective ingredients in the proper manner.

| Phase A | |
| --- | --- |
| $C_{12}$–$C_{15}$ alkyl benzoate | QS |
| UV filter $TiO_2$ | 20% |
| Phase B | |
| Isopropanol | QS |

-continued

| | |
|---|---|
| UV filters sodium and triethanolamine salts of 2-phenylbenzimidazole-5-sulfonic acid | 10.0% |
| Phase C | |
| Silicone oil | QS |
| Poly(dimethylsiloxane) g poly(isobutyl methacrylate) | 25% |
| UV filter oxybenzone | 10% |
| UV filter octyl methoxycinnamate | 5% |

The proportions of phases A, B and C in the total mixture were 30%, 20% and 50%, respectively.

EXAMPLE 4

(sunscreen as light make-up)

The individual phases were prepared separately by mixing the respective ingredients in the proper manner.

| | |
|---|---|
| Phase A | |
| $C_{12}$–$C_{15}$ alkyl benzoate | QS |
| UV filter $TiO_2$ | 5% |
| Zinc oxide | 2.5% |
| Kaolin* | 5.0% |
| Pigmented colors for make-up | 2.0% |
| Soluble colors | 1.5% |
| Phase B | |
| Shellac | 0.5% |
| Isopropanol | QS |
| UV filters sodium and triethanolamine salts of 2-phenylbenzimidazole-5-sulfonic acid | 15.0% |
| Phase C | |
| Silicone oil | QS |
| Poly(isobutyl methacrylate) co methyl FOSEA) g poly(dimethylsiloxane) | 20% |
| UV filter oxybenzone | 8% |

*Kaolin with a high kaolin content and 0.5–10 wt % spherical $SiO_2$ which has a particle size of <5 μm (according to [German] patent application P 44 45 064.8).

The proportions of phases A, B and C in the total mixture were 45%, 10% and 45%, respectively.

EXAMPLE 5

(light self-tanning agent with a high sunscreen factor)

| Liposome with DNA | |
|---|---|
| Lecithin | 10% |
| Dihydroxyacetone (DHA) | 10% |
| Ethanol | 7% |
| Water | QS |

The dihydroxyacetone is dissolved in water and stirred into lecithin. Then ethanol is stirred in and the entire mixture is homogenized well.

| | |
|---|---|
| Phase A | |
| Perfluorodecalin | QS |
| $TiO_2$ | 8% |

-continued

| | |
|---|---|
| Phase B | |
| Isopropanol | QS |
| Shellac | 1.5% |
| UV filters sodium and triethanolamine salts of 2-phenylbenzimidazole-5-sulfonic acid | 10.0% |
| Phase C | |
| PPG isostearyl ether | QS |
| UV filter butylmethoxydibenzoylmenthane | 5.0% |
| 4-methoxybenzylidenecamphor | 8.0% |
| Dihydroxyacetone liposome | 10.0% |

EXAMPLE 6

| | |
|---|---|
| Phase A | |
| Perfluorodecalin | QS |
| $TiO_2$ | 8% |
| Melanin | 1% |
| Phase B | |
| Ethanol | QS |
| Shellac | 1.5% |
| Sodium and triethanolamine salts of 2-phenylbenzimidazole-5-sulfonic acid | 15% |
| Phase C | |
| Jojoba oil | QS |
| Isohexadecane | 3% |
| Oxybenzone | 10% |
| Octyl methoxycinnamate | 15% |
| Melanin, soluble | 3% |

The proportions of phases A, B and C in the total mixture were 35%, 15% and 50%, respectively.

EXAMPLE 7

(make-up with self-tanning agent and a high sunscreen factor)

| | |
|---|---|
| Phase A | |
| $C_{12}$–$C_{15}$ alkyl benzoate | QS |
| UV filter $TiO_2$ | 5% |
| Zinc oxide | 1.5% |
| Kaolin* | 4.5% |
| Pigmented colors for make-up | 2.0% |
| Soluble colors, depending on tint | 1.0% |
| Melanin | 1.0% |
| DHA liposome according to Example 5 | 10% |
| Phase B | |
| Shellac | 1.0% |
| Isopropanol | QS |
| Sodium and triethanolamine salts of 2-phenylbenzimidazole-5-sulfonic acid | 15% |
| Phase C | |
| Silicone oil | QS |
| Poly(isobutyl methacrylate) co methyl FOSEA) g poly(dimethylsiloxane) | 20% |
| Oxybenzone | 8% |
| Vitamin E | 1% |
| Melanin, soluble | 1.5% |

EXAMPLE 8

Three mg of an oily phase (based on a linoleate) per $cm^2$ of skin were applied to ten volunteers. This phase contained 2% octyl methoxycinnamate (OMC) as a UV filter. Over this was applied 1 mg/cm$^2$ of an aqueous phase. The aqueous phase contained 3% Tio$_2$, so that 4 mg/cm$^2$ contained a total of 0.14 mg OMC/cm$^2$ and 0.2 mg TiOVEIL AQN/cm$^2$. According to measurement of the sunscreen factor by the Diffey method, an average sunscreen factor of 7.03 was obtained.

Comparative Example 1

A comparative emulsion was applied to ten volunteers in the amount of 4 mg/cm$^2$. The emulsion contained 1% titanium dioxide filter and 1.5% of the OMC filter. This comparative emulsion thus contained the same amount of UV filter as the two layers in Example 8 together. According to measurement of the sunscreen factor by the Diffey method, an average value of 4.97 was obtained.

The comparison shows clearly that even a two-layer arrangement of sunscreen agents permits a significant improvement in comparison with the known emulsions.

We claim:

1. A multi-phase sunscreen agent, comprising
at least two phases that are selected from the group consisting of liquid, pasty and gelatinous which are separated from each other spontaneously within seconds up to less than ten minutes after a brief and gentle mixing process lasting less than one minute without any essential application of force, wherein at least one of the phases in an oily phase, and another phase in a non-oily phase containing a perflurorcarbon or a perfluorocarbon mixture, and where at least one phase contains a UV filter.

2. A sunscreen agent according to claim 1,
comprising at least two essentially liquid phases that are separate from each other, where at least two of the phases contain at least one UV filter each, and the phases separate spontaneously after a brief and gentle mixing process, leaving the respective UV filters in the phases in which they were originally present, and the phases form separate layers.

3. A sunscreen agent according to claim 2,
wherein at least three essentially liquid phases that are separate from each other, where at least two of the phases contain one UV filter each, and the phases separate spontaneously after a brief and gentle mixing process and form separate layers.

4. A sunscreen agent according to claim 1, wherein the oily phase contains a dissolved or suspended lipophilic sunscreen agent.

5. A sunscreen agent according to claim 4, wherein the lipophilic sunscreen agent is a UV filter selected from the group consisting of phenylbenzimidazolesulfonic acid salts, a salicylic acid ester, a benzophenone, a cinnamic acid ester, a benzomalonic acid ester, a triazine, a dibenzoylmethane derivative and dihydroxyacetone.

6. A sunscreen agent according to claim 1, wherein the phases do not contain any water.

7. A sunscreen agent according to claim 1, wherein the non-oily phase contains a suspended or dissolved hydrophilic sunscreen agent.

8. A sunscreen agent according to claim 7, wherein the UV filters used as the hydrophilic sunscreen agent are selected from the group consisting of titanium dioxide, zinc oxide and a mixed oxide selected from the group consisting of (a) of TiO$_2$ and SiO$_2$ or Al$_2$O$_3$, TiO$_2$ and SiO$_2$, and (b) of ZnO and SiO$_2$ or Al$_2$O$_3$ and ZnO and SiO$_2$.

9. A sunscreen agent according to claim 5, wherein
the lipophilic sunscreen agent is a UV filter selected from the group consisting of 2-hydroxy-4-methoxybenzophenone, 2-ethylhexyl p-methoxycinnamate, sodium and triethanolamine salts of 2-phenylbenzimidazole-5-sulfonic acid, oxybenzone and dihydroxyacetone.

10. A sunscreen agent according to claim 3, comprising three phases, where
phase (A) comprises one or more perfluorocarbons and an inorganic oxide or oxide mixture distributed in it as the UV filter; and
phase (B) comprises a polymer film-forming compound or a polymer lac in an organic solvent, optionally in mixture with a UV filter; and
phase (C) comprises at least one cosmetically acceptable oil and at least one lipophilic UV filter contained in it.

11. A sunscreen agent according to claim 10, wherein the proportion of phases, based on the total consumption, is 15 to 35 wt % phase (A), 5 to 25 wt % phase (B) and 25 to 80 wt % phase (C).

12. A sunscreen agent according to claim 10, wherein the organic solvent is an alcohol.

13. A sunscreen agent according to claim 10, wherein the polymer lac is shellac.

14. A sunscreen agent according to claim 10, further comprising phase (D) comprising an oil different from phase (C) and optionally a lipophilic UV filter.

15. A sunscreen agent according to claim 1, wherein the phases are contained in a dispenser in which they are spatially separated.

16. A sunscreen agent according to claim 15, wherein the phases are present in the dispenser in proportions that correspond to their predetermined mixing ratios.

17. A process for applying a sunscreen agent to the skin, comprising
providing essentially liquid and anhydrous phases which are spatially separated in a dispenser and comprising at least:
(1) an oily phase containing a UV filter,
(2) a phase with a polymer lac or film-forming agent and optionally a UV filter, and
(3) a phase containing one or more fluorocarbons and a UV filter
mixing together said phases in predetermined mixing ratios immediately before application and applying said phases to the skin in mixed form and distributed there, so that separate layers are formed on the skin.

18. A process according to claim 17, further comprising incorporating one or more inorganic pigments as UV filter(s) into the phase which forms a layer on the skin and comes in direct contact with the skin.

19. A sunscreen agent according to claim 12, wherein the alcohol is isopropanol or ethanol.

* * * * *